United States Patent [19]

Paau et al.

[11] Patent Number: 4,556,643

[45] Date of Patent: Dec. 3, 1985

[54] ASSAY METHOD AND PROBE FOR POLYNUCLEOTIDE SEQUENCES

[75] Inventors: Alan Paau, Middleton; Steven G. Platt; Luis Sequeira, both of Madison, all of Wis.

[73] Assignee: Agracetus, Middleton, Wis.

[21] Appl. No.: 462,719

[22] Filed: Feb. 1, 1983

Related U.S. Application Data

[63] Continuation-in-part of Ser. No. 401,957, Jul. 26, 1982, abandoned.

[51] Int. Cl.[4] .................... G01N 33/50; G01N 33/54; C12Q 1/68; C12Q 1/70; C12Q 1/29; C12Q 1/04; C12Q 1/06
[52] U.S. Cl. .................... 436/501; 436/504; 436/63; 436/94; 436/518; 436/530; 435/6; 435/5; 435/7; 435/29; 435/34; 435/39; 935/78
[58] Field of Search .................... 435/5, 6, 7, 29, 34, 435/39; 436/63, 94, 501, 504, 518, 530

[56] References Cited

U.S. PATENT DOCUMENTS 4,446,237   5/1984   Berninger .................... 435/6

FOREIGN PATENT DOCUMENTS 2019408   10/1979   United Kingdom .................... 435/6

OTHER PUBLICATIONS

Strauss et al: Biochemistry 19, 3504, (1980).
Moeller et al: Chem. Abstr. 97:179913c, (1982) of J. Biol. Chem., 257, 12081, (1982).
Hsieh et al: Proc. Natl. Acad. Sci. USA 76, 726, (1979).
Weber et al: in *The Operon*, Reznikoff (ed.), Cold Spring Harbor Laboratory, 1980, pp. 155-175.
Grunstein et al: Proc. Natl. Acad. Sci. USA 72, 3961, (1975).
Langer et al: Proc. Natl. Acad. Sci. USA 78, 6633, (1981).
Barkley et al: in *The Operon*, Reznikoff (ed.), Cold Spring Harbor Laboratory, 1980, pp. 177-220.
Strauss et al: Biochemistry 19, 3496, (1980).
Saito et al: Biochim. Biophys. Acta 72, 619, (1963).
Kislev et al: Plant Physiol. 66, 1140, (1980).
Kemble et al: Genetics 95, 451, (1980).
Murray et al: Nucleic Acid Res. 8, 4321, (1980).
Gerlach et al: Heredity 44, 269, (1980).
Miura: Methods Enzymol. 12, 543, (1967).
Marmur: J. Mol. Biol. 3, 208, (1961).
Thomas: Proc. Natl. Acad. Sci. USA 77, 5201, (1980).
Bartnik et al: Anal. Biochem. 116, 237, (1981).
Higuchi et al: Proc. Natl. Acad. Sci. USA 73, 3146, (1976).
Pratt et al: What's New in Plant Physiology 9, 1, (1978).

*Primary Examiner*—Blondel Hazel
*Assistant Examiner*—James Martinell
*Attorney, Agent, or Firm*—Albert P. Halluin; Elliott Fineman; Nicholas J. Seay

[57] ABSTRACT

An assay method for the detection of a specific nucleotide target sequence in a polynucleotide test extract is disclosed which utilizes a polynucleotide modified probe including both a cDNA sequence substantially complementary to the specific target sequence and a protein binding sequence. The assay is conducted by exposing the modified probe to the polynucleotide test extract for hybridization and then exposing the complex to the protein which binds to the protein binding sequence. An assay, such as an immunoassay, can then be conducted on the test sample to indicate the presence of the specific target sequence by detecting the presence of the binding protein.

24 Claims, No Drawings

ASSAY METHOD AND PROBE FOR POLYNUCLEOTIDE SEQUENCES

CROSS REFERENCE TO RELATED APPLICATION

This application is a continuation-in-part of Ser. No. 401,957 filed July 26, 1982, now abandoned.

TECHNICAL FIELD

The present invention relates generally to assay methods for samples of polynucleotides. In particular, the present invention relates to a method for conducting a qualitative or quantitative assay for the presence of a specific target nucleotide sequence in a sample polynucleotide extract of unknown or uncertain content and to a probe for use in such an assay.

BACKGROUND OF THE INVENTION

Generally in the technology of manipulating genetic material or in evaluating the genetic character of an organism, it is often desirable to ascertain if a particular gene or part of a gene is present in an organism or in an extracellular extract of genetic material from an organism. Since any gene or gene portion is, in essence, a specific sequence of nucleotide bases forming all or part of a polynucleotide molecule, to discover if a particular gene or gene fragment is present in a sample, it is possible to directly test the sample polynucleotide to discover if the specific sequence of nucleotide bases forming the gene is present in the sample.

The present method generally used for detection of a specific nucleotide target sequence in a DNA or RNA polynucleotide sample depends upon the hybridization of a sample, referred to as a test sequence, to a radioactively labeled complementary DNA probe containing the target sequence. The cDNA probe may be isolated in quantity or may be cloned using known techniques, such as by insertion into a DNA vector, either a plasmid or a phage, which is inserted into a bacterium propagated in a nutrient medium. If the media includes a radioactive isotope which is absorbed by the bacterium into its own DNA, such as $^{32}P$, the cloned DNA probe includes a radioactive component therein. Alternatively, the isolated DNA probes may also be labeled radioactively by in vitro chemical reaction. In the detection procedure, the test sequence, which is typically immobilized on a filter, is exposed to the radioactively labeled complementary DNA probe, after which the test sequence is then washed. A radioactive assay of the test sequence is then conducted by a scintillation specmeter or by autoradiography. The amount of radioactive isotope detected by the radioactive assay is indicative of the amount of the radioactive cDNA probe which has been hybridized to the test sequence, and is therefore an indication of whether the test sequence includes the target sequence which is sought.

While assay methods utilizing radioactively-tagged polynucleotides are effective for the assay of such sequences, there are several disadvantages inherent in such procedures. The radioactive materials which are required are inherently somewhat hazardous, and are also inherently unstable. Furthermore a laboratory performing such an assay procedure must be specially licensed and have specially trained technicians in order to use radioactive materials. Many laboratories may be unable to conduct such assays because of the burdensome nature of the safeguards encumbent in the use of such materials and the special licensing procedure required by it. The assay method of the present invention is, in part, intended to avoid the use of radioactive materials.

SUMMARY OF THE INVENTION

The present invention is summarized in that a method for assaying for the presence of a specific target nucleotide sequence in a sample polynucleotide test extract includes the steps of first isolating the test extract as a test sample, then exposing the test sample to: (1) a modified probe including both a cDNA sequence substantially complementary to the target nucleotide sequence and a protein binding sequence adapted to bind to a predetermined protein, (2) a binding protein which will bind to the protein binding sequence of the modified probe. After the test sample has been washed to remove unreacted constituents, an assay of the test sample for the presence of the binding protein is conducted. Such an assay of the test sample is preferably a direct or indirect marker-linked immunoassay utilizing any known marker type, such as enzymes, flourescent groups, lysisinitiating groups or any other suitable non-radioactive marker moities.

It is thus an object of the present invention to provide a method for the detection of a specific target nucleotide sequence in a sample polynucleotide test extract by a marker-linked assay, possibly amplified, so that the presence of the specific nucleotide target sequence can be ascertained without the need for radioactive materials.

Another feature of the present invention is a modified polynucleotide probe which is usable in a polynucleotide assay procedure, the modified probe including both a cDNA sequence substantially complementary to the target sequence and a protein-binding sequence in a common molecule.

Yet another feature of the present invention is that the protein-binding sequence and the cDNA sequence may be one and the same sequence if a specifically antigenic nucleotide is incorporated into the cDNA sequence.

Utilizing the assay method of the present invention, it is possible to detect specific target nucleotide sequences in either the DNA or RNA of any organism. Thus the technique can be used for diagnosis or identification of pathogens or non-pathogens for disease diagnosis, or of viruses, viroids, bacteria, fungi, protozoa, or any other plant or animal life form. In addition, the method can be used to assay segments of DNA, RNA, or mRNA segments in or from newly bred organisms to verify the presence of gene sequences which have been introduced into the organism either through conventional breeding techniques or through genetic manipulation. The method can be utilized to determine the presence of a target gene of specific interest, or its mRNA transcription, in cells of a host without requiring growth of the life form to a stage at which phenotypical expression of the gene occurs. This is especially useful in a breeding program, such as for plants, in that it makes possible a screening assay for selection of the breeding stock at an early stage to allow immediate discarding of all progeny which do not include the desired trait. In addition, the assay method can be used to determine the presence or absence of any identified gene in animal cells, or in human cells, regardless of whether or not the phenotype is expressed in the individual in question. Thus the method may be applicable to detection of genetic disease or to the detection of recessive genetic trait carriers in individuals in whom the gene is not expressed.

Other objects, advantages, and features of the present invention will become more apparent from the following detailed description.

BRIEF DESCRIPTION OF THE DRAWING

The single drawing FIGURE is a summary flow sheet illustrating a method for assaying the presence of a specific target nucleotide sequence in a sample polynucleotide test extract in accordance with the present invention.

DETAILED DESCRIPTION OF THE INVENTION

The assay method of the present invention involves exposing an isolated sample of the test polynucleotide to a series of reagents. To best understand the operation of the procedure, the method of preparation and contents of the assay materials will be discussed first, followed by a description of the assay method steps.

1. Preparation of Assay Materials.

The first major material which must be prepared for the present assay procedure is a cloned DNA probe strand which includes both a cDNA sequence substantially complementary to the target sequence, and a protein-binding sequence, in a common molecule. The probe strand is referred to herein as the "modified probe". To prepare the modified probe it is necessary to be able to create and isolate the cDNA sequence for the specific target nucleotide sequence to be assayed.

To prepare the cDNA sequence, it is first necessary to isolate a sample of the specific nucleotide target sequence which the assay is intended to detect. To isolate a sample extract of the target sequence, a procedure such as that discussed below with reference to the test extract can be utilized. Alternatively if the nucleotide sequence of the target sequence is fully known, it is possible to synthesize the sequence directly. The cDNA sequence can then be prepared by transcription from the polynucleotide including the target sequence. The means for identifying the target sequence and for preparing and isolating the cDNA sequence are not critical and any means recognized in the art may be used for this part of the procedure. Preferably, the cDNA strand is then inserted into a cloning vector using any of a number of published techniques.

One advantageous method for both creating the cDNA sequence and inserting it into a cloning vector is documented by Haguchi et al., *Proc. Natl. Acad. Sci. USA* 73: 3146–3150 (1976). In this procedure, a reverse transcriptase is utilized to create a cDNA complementary strand in which each of the nucleotides is the complement to the nucleotide in the target sequence. Then the cDNA strand thus created is treated first with an exonuclease and then with terminal transferase which is reacted in the presence of a sole nucleotide to create a specific homopolymeric tail sequence on the cDNA strand. That homopolymeric tail sequence is matched to a complementary homopolymeric tail sequence created through a similar process in a polynucleotide plasmid or phage vector which is then inserted into a bacterium for cloning.

Several procedures for inserting such DNA or cDNA fragments into vectors which are then inserted into bacteria for cloning are well documented in the literature. In the procedure at hand, the vector, which may be a plasmid or a phage, including the cDNA sequence is cloned in a bacterium to generate a number of daughter polynucleotide strand clones, including the cDNA sequence, which can be utilized in the formation of the modified probe. This same procedure is used to create the cDNA sequence complementary to any DNA, RNA, or mRNA sequence, regardless of whether the sequence is an entire gene, a portion of transcript of a gene, an operon, a promotor, an intron, or any other nucleotide sequence.

After the cDNA probe has been cloned, the clone, or a segment of the cloned strand including the cDNA strand, is then modified to carry an additional DNA sequence which is specifically intended to bind to a certain protein. For purposes of the present invention, the sequence is referred to as a protein-binding sequence, and the protein that binds to it is referred to as a binding protein. The method using for joining the protein binding sequence to the cDNA sequence is not unduly critical as long as the two sequences are active for their respective purposes and are bound together. This joining operation may be accomplished through any recognized means such as blunt end ligation, sticky end ligation, or other ligation procedure or even through the use of an adaptor coupling moeity joined to each strand. One method to accomplish this modification of the strand including the cDNA probe, is a method wherein the strand is cut with a restriction endonuclease, or has its end modified using either synthetic linkers or by addition of a homopolymeric tail sequence to create a strand with a sticky end. The sequence of DNA carrying the protein binding sequence is similarly isolated and modified also using a restriction endonuclease or other method to be complementary to the sticky end of the cDNA strand. The segment containing the protein binding sequence is then bound to the segment containing the cDNA to create the modified probe. Either this modified probe is an entire vector by itself, or the modified probe is then inserted into a vector to create a modified vector. The modified vector is then inserted into a bacterium to create a series of cloned modified probes.

As an alternative to the above described procedure in which the cDNA strand is inserted into a vector and then cloned before the protein binding sequence is also inserted into the cloned vector, it is also envisioned that the order of insertion of the two sequences into the cloning vector can be reversed. For example, it would be possible to first isolate a protein binding sequence, through the use of an appropriate restriction endonuclease or other cleavage method, and then to insert the resultant protein binding sequence strand into the cloning vector. Either before or after the vector has been cloned, although it is preferable to conduct an initial cloning of the vector containing the protein binding sequence to have more material to work with, the cDNA strand is inserted into the vector, which is then additionally cloned. Thus the order in which each of the two sequences is introduced into the modified vector is less important than the fact that both are introduced into the same vector to create the modified probe in that vector. It is also possible to utilize a vector, either a plasmid or a probe, which already includes a protein binding sequence in it. Then it is merely necessary to insert the cDNA sequence into the vector for cloning to create the modified probe in the vector. The cloning procedure itself would not be necessary if quantities of the cDNA sequence and the protein binding sequence were able to be isolated directly and then bound to each other.

Several categories of protein binding sequences capable of being utilized in the method of the present invention are presently known and methods for isolating and utilizing these protein binding sequences have been published. For example, the expression of a structural gene of an organism is often modified or controlled by a set of operon regulations on regulator and operator control genes which can either inhibit or promote the synthesis of the proteins coded by the structural genes. Among the control genes is often found a promoter sequence which is a specific site for the binding of RNA polymerase to facilitate the initiation of the transcription of an mRNA molecule from the structural gene. Such a promoter, therefore, has an affinity to bind to RNA polymerase, a protein enzyme. The lac-promoter and trp-promoter sequence of *E. coli* have been extensively studied, cloned in vectors, and are well-identified. The sites for restriction endonuclease cleavage adjacent to those promoters and, in fact, the nucleotide sequence of those promoters, have also been published. Therefore, it is known how to isolate and clone DNA fragments including those promoter sequences. It is also possible to synthesize such a protein binding sequence in its entirety if the base sequence of the promoter has been identified, as it has been for the lac promoter and trp promoter sequences.

Similarly, other control sites on DNA strands having an effect on the expression of structural genes can also be utilized as a protein binding sequence. For instance, several operon segments have been identified in *E. coli* which inhibit expression of structural genes with which they are associated. One such operon segment is in the operon including the lac operator, which is inhibited when the segment is bound to a protein called the lac repressor. Thus this operon segment which binds to the lac repressor is also a suitable protein binding sequence.

Other useful protein binding sequences are the promoters associated with bacteriophage activity. Bacteriophages, such as the T5 and T7 bacteriophages, include strong promoter sequences which also bind preferentially to an RNA polymerase in the organism they infect so as to initiate protein synthesis of the proteins encoded by the genes of the phage. Thus the DNA strands of the phages or portions of the strands including the strong promoter sequences can serve as effective protein binding sequences to RNA polymerases which are isolated from the organisms which the phages infect.

Another class of useful protein binding sequences are sequences of nucleotide materials which are specifically antigenic. Generally, DNA sequences are very mildy antigenic and any anti-serum prepared for a DNA sequence is not specific to that sequence. However, certain nucleotide sequences are specifically antigenic and such sequences are usable as the protein binding sequence in the modified probe of the present invention. This specifically antigenic sequence may be included directly in the cDNA sequence, or may be carried in a separate part of the modified probe. Two examples of specifically antigenic nucleotide sequences are a Z-DNA sequence and a sequence containing a specific rare nucleotide.

One type of specifically antigenic sequence which may be used as protein binding sequence is Z-DNA. Z-DNA is an isomer of DNA which includes a series of base pairs (poly dGdC) which thermodynamically favors the formation of a left handed helical strand, rather than the right handed helix of most DNA. Z-DNA is useful as a protein binding sequence since it is both antigenic and relatively rare in nature. The antigenic property of Z-DNA allows an antiserum to be prepared which binds to Z-DNA and not to normal DNA, and the fact that Z-DNA is relatively rare lowers the rate of false positive indications. Generally DNA is very mildly antigenic and an anti-serum prepared for it is not specific to any sequence. Thus the use of Z-DNA as the protein binding sequence provides a nucleotide sequence which can be recognized by an antiserum and avoids the problem of non-specificity since Z-DNA is so rare and anti-Z-DNA antiserum does not recognize usual right handed DNA.

Another type of specifically antigenic sequences which is usable as the protein binding sequence within the present invention is any nucleotide sequence including therein a rare and antigenic nucleotide, such as five-bromodeoxyuridine and five-iododeoxyuridine. These two rare nucleotides are examples of nucleotides which rarely occur in nature but which may be freely incorporated into a nucleotide sequence in the same fashion as a conventional nucleotide. The halogen constituent in these nucleotides makes possible the generation of an antiserum specific to these rare nucleotides. Since the nucleotides are very rare in any natural sequence, the antiserum is specific to any sequences containing the rare nucleotides to a very high degree. To make use of this feature, the probe which contains the cDNA sequence complementary to the target sequence can be propagated in a host grown with a special medium that contains these rare nucleotides. This process will produce, in vivo, a modified probe that can hybridize to the target sequence and which also contains integrally therein a specifically antigenic sequence, that being the sequence which contains the rare nucleotide. Thus an antiserum to the rare nucleotides will bind to that sequence. The specifically antigenic sequence, functioning as the protein binding sequence, can be incorporated directly into the cDNA sequence, or it can be incorporated into a separate sequence on the modified probe. Monoclonal antisera against the rare nucleotides and the Z-DNA are preferred, although not required, if a specifically antigenic nucleotide sequence is to be used.

In general, it is envisioned that any sequence of nucleotides contained in a DNA fragment is capable of serving as the protein binding sequence for the method of the present invention if the sequence is capable of being isolated and inserted into a cloning vector, and if the sequence has an affinity to bind to a binding protein with specificity and if the specified binding protein is capable of being detected by an assay procedure. Since it is preferred, if Z-DNA is not used, to conduct an immunoassay for the binding protein, it is preferred that the binding protein be capable of causing an antigenic reaction in an animal of another species. If a specifically antigenic sequence, such as Z-DNA or a rare nucleotide sequence is used as the protein binding sequence, the protein binding sequence may possibly be present naturally in the cloning vector or can be created by in vivo or in vitro incorporation of the specifically antigenic sequence and nucleotides into the cloning vector, either as a separate sequence, or as part of the cDNA sequence.

The selection of the binding protein to be used as a reagent in the method of the present invention depends, of course, on the selection of the protein binding sequence. The only essential criteria for selection of the binding protein is that it is required that the binding protein have an affinity to bind to the particular protein binding sequence selected with selectivity and, if an immunoassay is used it is required that the protein be capable of causing an antigenic reaction in an animal of another species. It is also possible to use complexes of proteins to other substances, such as a protein-hapten complex, a protein-enzyme complex, or any other protein-marker complex as the binding protein. An RNA polymerase is a particularly appropriate protein to utilize in this process since it has an affinity to bind to many promoter sequences associated with many structural genes, and thus many protein binding sequences are available which are specific to this protein. Furthermore, since the procedures for the isolation of RNA polymerase and of appropriate promoter sequences have been extensively studied and published, these are particularly appropriate materials to utilize within the method of the present invention. The lac repressor, a protein complex, is also particularly well documented and usable in this procedure. If a specifically antigenic sequence is used as the protein binding sequence, the binding protein is preferably an antiserum specific to the specifically antigenic sequence or such as antiserum linked to a non-radioactive marker, such as an enzyme. Other binding proteins useable in the procedure of the present invention include other repressors, histones, DNA modifying enzymes and polymerases, and other activator proteins such as the catabolite gene activator protein (CAP).

It is envisioned that detection of the binding protein may be accomplished by any known assay method capable of detecting the binding protein. It is preferred, however, except if an antiserum specific to the specifically antigenic protein is the binding protein, that the protein be detected through an immunoassay, because of its specificity and sensitivity. To conduct such an immunoassay, it is necessary to prepare an antiserum specific to the binding protein. The antiserum is prepared and isolated in a conventional fashion known in the art from a rabbit or other animal. The foreign binding protein is injected, as an antigen, into the animal over a time frame sufficient to cause a maximal antigenic reaction in the animal. The serum is then be retrieved from the animal and the antiserum specific to the binding protein is isolated for later use. If a direct immunoassay procedure is to be used, as discussed below, then the antiserum is linked to any one of the markers conventionally used in marker-linked immunoassays, for instance enzymes such as peroxidase or alkaline phosphatase or flourescent markers, such as flourescein. It is possible, and is preferred, that multiple markers be joined to the antiserum to amplify the marking effect in a manner well known in the art.

If an indirect immunoassay is to be utilized in conjunction with the method of the present invention, a reagent including a second antiserum is necessary. For the second antiserum goat anti-rabbit IgG, created in a fashion similar to the preparation of the antiserum for the binding protein, can be used. The second antiserum is then linked with a marker such as the enzymes peroxidase, B-galactosidase, or alkaline phosphatase, or a flourescent marker such as flourescein, or any other moiety capable of being detected through a visible assay. It is also possible to utilize the goat anti-rabbit IgG without the linkage of any enzyme thereto and then to also utilize a commercially available PAP complex (peroxidase-rabbit anti-peroxidase) in a double indirect assay procedure as will be described below.

2. The Method.

The method of assaying for the presence of a specific nucleotide target sequence in accordance with the teachings of the present invention will now be described. Reference numerals refer to steps illustrated in the flow chart in the attached drawing FIGURE.

The procedure begins with the isolation and immobilization of a sample of the test polynucleotide extract. To prepare the test sample of the test extract for the assay, a sample of genetic material, or a sample of other cell material including the genetic material, is homogenized, and, if necessary, purified. An aqueous extract of the sample is then prepared in such a manner that the polynucleotides in the extract can be immobilized, for example by deposit onto a nitrocellulose filter or other insoluble matrix. The aqueous extract is preferably buffered to a neutral to alkaline pH. Several procedures are known for the isolation of such polynucleotide samples and the procedures typically include deproteinization of the extract through the use of phenol and chlorofor-misoamyl alcohol extracts in high salt concentrations. The isolation of the extract is preferably by immobilization onto a nitrocellulose filter, but may also be by immobilization onto any other solid filter support or other support media or other insoluble matrix. Any other nucleotide isolation or immobilization procedure may also be used. The sample polynucleotide test sequence as immobilized on the matrix is referred to as a test sample hereafter. The immobilization step is illustrated at 11 in the drawing FIGURE.

The polynucleotide test extract which is to be assayed may be from any life form, including microorganisms, bacteria, viruses, viroids, and plant or animal tissue. To prepare a test sample extract of a micro-organism polynucleotide, the micro-organisms can be captured directly on filters and then lysed either with a detergent (i.e. sodium lauryl sulfate), or an enzyme (e.g. lysozyme). The polynucleotides can then be separated from the balance of the cellular material. For plant or animal tissue, a mechanical homogenation of the plant or animal tissue through the use of a mortar and pestle or a Waring blender can be performed, again followed by treatments with detergents or enzymes and a separation process. Several teachings are available of various methods detailing the preparation of bacterial, plant, or animal extracts suitable for immobilization of polynucleotide extracts on filters, such as Saito et al. *Biochim. Biophys. Acta,* 72 (1963) 619–629, Kislev et al., *Plant Physiology,* 66: 1140–1143 (1980), Kemble et al. *Genetics,* 95: 451–458 (June, 1980), and Murray, et al., *Nucleic Acids Research,* 8: 19, 4321–4325 (1980).

While it is possible, and generally preferable, to utilize a relatively pure extract of polynucleotides in the method of the present invention, it is also possible to use an impure extract within the method of this invention as long as the impurities present in the extract are not of a nature so as to react with the other reagents used in the process. Typically, the use of organelles from the cells which contain polynucleotide sequences of interest will not include excess amounts of impurities which will effect the validity of the process.

The extract of the test polynucleotide can be immobilized on a nitrocellulose filter through the use of any of the established procedures, such as "Southern Blot", "Northern Blot", or "Dot Blot". These procedures typically involve denaturing the sample nucleic acids by heat, or by alkaline or other chemical treatment, (e.g. glyoxal and methyl-mercury chloride treatment) followed by noncovalent bonding to the nitrocellulose filter. It is also envisioned that matrix materials which form covalent bonds to the nucleotide extracts, as for instance DBM paper, may be utilized. As stated above the choice of the matrix is not critical as long as the test extract can be immobilized in the matrix and as long as the matrix is capable of binding the test extract throughout the balance of the procedure.

The polynucleotides in the sample test extract to be assayed may be entire polynucleotide strands, forming intact DNA molecules, or may be entire RNA molecules, or entire mRNA molecules, or may be polynucleotide fragments of any length created by restriction enzyme cleavage or any other cleavage of any DNA or RNA molecules.

After the immobilization of the test sequence on the filter, a pre-hybridization wash 12 with a buffer solution is preferably performed to remove any unnecessary impurities from the sample and to saturate all nonspecific binding sites on the matrix.

After the step of immobilizing the sample nucleotide extract as a test sample, and the pre-hybridization wash, the next step in the method is to expose the test sample to the denatured modified probe for hybridization. The procedure of creating the modified probe, described above, is indicated at 13 in the drawing FIGURE. In the hybridization procedure 14, the test sample is immersed in a buffer solution to which is added a stoichiometric excess the denatured modified probe. A stoichiometric excess of the denatured modified probe is used to insure that sufficient amount of the modified probe is available for hybridization to each of the polynucleotide strands contained in the sample extract which include the target sequence. Procedures for conducting such a hybridization are known. See for example Thomas *Proc. Natl. Acad. Sci.* USA, 77: 9:5201–5208 (1980) and Denhart *Biochem. and Biophys. Comm.*, 23:641–6 (1966). Successful hybridization will occur only if the nucleotide sequence of a portion of the sample nucleotide test extract matches a corresponding complementary nucleotide target sequence in the modified probe. Thus, if in the sample test polynucleotide extract there is a strand having the target sequence, the cDNA sequence from the modified probe will hybridize to that target sequence and a double stranded complex will be formed. Some sections of the cDNA strands in the solution may hybridize to other cDNA sequences contained on other strands of the modified probe to form complexes of interconnected strands of the modified probe. If any one of the cDNA sequences among the interconnected strands binds to one of the strands in the test sample, the entire complex is thereby attached to the test sample. Since the sample test extract is immobilized, any such complexes or any single strands of the modified probe containing the cDNA sequence which binds to the sample will also be immobilized. Any such strand of the modified probe which is so immobilized will also include a protein binding sequence.

It should be understood that exact complementarity is not required between the cDNA sequences and the test sequence. Hybridization will occur even if there is a significant number of mismatched base pairs, in some cases 30% or more. By varying the stringency of the hybridization procedures it is possible to require more, or less, complementarity for hybridization.

Following the hybridization, a post-hybridization wash 15 is conducted to rinse any excess unhybridized excess of the modified probe, not bound directly or indirectly to the test sample, off of the test sample. The post-hybridization wash is accomplished with a buffer solution.

The next step in the procedure is to expose the test sample to the binding protein. The test sample is exposed to a solution including the binding protein therein. The solution must contain the binding protein, and the sample must be held under conditions which promote the binding of the binding protein to the protein binding sequence in the modified probe, if it is present. If any modified probes have been bound to the immobilized sample polynucleotide test extract, the portion of the modified probe containing the binding sequence is still in the test sample. If the protein binding sequence is present in the test sample, the binding protein is then bound to the protein binding sequence and immobilized in the test sample. The protein binding step, indicated at 16 in the drawing, should also include an excess amount of the binding protein to insure complete binding.

After the binding procedure, the excess binding protein is washed away from the filter. This post-hybridization washing operation, indicated at 17, should utilize a buffer solution which will not disturb the complex which may have been formed between the immobilized test polynucleotide sample bound to the modified probe which in turn is bound to the binding protein.

If the cDNA sequence substantially matches the sequence of one or more strands contained in the sample polynucleotide extract, the test sample now contains, on the matrix, a complex including the sample extract, one or more strands of the modified probe, and binding protein bound to the modified probes. An assay is now conducted for the presence of the binding protein. One method of detecting the binding protein is to bind a marker moiety, such as an enzyme or flourescent, directly to the binding protein. For example, if anti-Z-DNA antiserum is used as the binding protein, a peroxidase can be bonded directly to the antiserum and the presence of the protein detected by testing for the enzyme. Any other non-radioactive method may be used to detect the binding protein, but an immunoassay for the protein is preferred, and that procedure will be described in detail.

For a direct immunoassay, the test sample is then exposed to an aqueous solution, such as a phosphate buffered saline solution, of the antiserum prepared against the binding protein. Since the antiserum is specific to the binding protein, the antiserum will bind to this complex contained in the test sample only if the binding protein is present in the complex. The antiserum binding step is indicated at 18. If no portion of the sample test polynucleotide extract matched the cDNA in the modified probe, the modified probe would not have adhered to the test sample, the binding protein would thus have not also adhered to the test sample, and at this stage the antiserum would find no binding protein against which to bind. By contrast, if the complex has been formed, the antiserum would also bind to the complex. Following this reaction, excess antiserum is washed 19 from the test sample by a buffer, such as, again, a phosphate buffered saline solution.

At this antiserum binding step in the procedure, it is possible to utilize an antiserum specific to the binding protein to which a marker such as an enzyme or a flourescent marker has been linked. If such a marker-linked antiserum is used, the test sample is now ready for an appropriate assay for presence of the marker linked to the antiserum. Suitable enzymes which may be utilized for linkage to the antiserum as a marker include alkaline phosphotase, peroxidase, and $\beta$-galactosidase. This direct immunoassay, as indicated at 20, is only one of many methods to assay for the presence of the antiserum, however.

Alternatively, if the antiserum specific to the binding protein is not linked to a marker, a conventional indirect or double indirect marker-linked immunoassay can be undertaken to detect the presence of the antiserum to the binding protein. Such indirect and double indirect immunoassays and variations of them are well known and documented in the art. An indirect assay uses an antiserum, like goat anti-rabbit IgG, which is specific to the antiserum, i.e. rabbit IgG, used to bind to the protein, where the marker is attached to the second antiserum, i.e. the goat anti-rabbit IgG. A double indirect assay uses both these two antisera, neither marker linked, and then uses a marker linked antiserum, i.e. peroxidase-rabbit antiperoxidase (PAP), which is marked, i.e. with an enzyme, and which binds to the second antiserum. The advantage in the use of such indirect or double indirect assays is that the second antiserum is general to all antisera from the species from which the first antiserum ws generated. Such marker-linked antisera are also commercially available. More than one marker can be attached to each IgG molecule, also, to amplify the assay results. It is conventional for such procedures to give a visual indication, through a reaction catalyzed by the marker enzyme linked to the antiserum, as to the presence of the protein which the assay seeks to detect. It is also possible to utilize a flourescent marker such as fluorescein linked to the antiserum, instead of an enzyme, to detect the presence of the target sequence, or any other marker moiety. If such a fluorescent marker is utilized, the test sample, after washing, is exposed to UV illumination with the level of resulting fluorescence being a direct indication of the amount of the specific nucleotide sequences present in the test sample extract.

Thus the method of the present invention makes possible an assay of any RNA or DNA sequences which does not involve the use of radioactive nucleic acid probes. Thus the disadvantage inherent in the use of such radioactive probes are avoided. The procedure results in a protein-nucleotide complex which can be detected by any method suitable for protein detection such as through a marker-linked immunoassay, a well known procedure which is widely used for the detection of antigenic proteins. Such a procedure is not normally available for the detection of polynucleotide sequences since nucleic acids, other than Z-DNA, generally are minimally antigenic and antisera to nucleic acids are generally non-specific to particular sequences. The method of the present invention combines the advantages of the specificity of polynucleotide hybridization and the sensitivity of protein detection assays such as marker-linked immunoassays to create a single assay procedure for polynucleotide sequence which is thus both very specific and very sensitive and which can detect polynucleotide sequences. The method is accomplished by utilizing the modified probe which contains both the cDNA sequence, which gives rise to the specificity, and also the protein binding sequence, which allows the process to take advantage of the sensitivity of any protein detection assay procedure. Thus the procedure provides extremely high sensitivity but is still very selective, and does not involve the use of any hazardous materials requiring special license or special handling.

Another advantage of the present procedure is that many of the reagents utilized in the procedure can be common to many assays and thus can be prepared in bulk for their use in a number of assay procedures. Except for the cDNA sequence, which is specific to the specific nucleotide sequence which is sought to be detected, the remaining components and reagents utilized in the procedure can be standardized. For instance, it would be possible to insert the protein binding sequence into a cloning vector and to create a reasonable supply of such vectors, including the protein binding sequence therein, and similar stocks of the binding protein, marker-linked binding protein, or of the antiserum specific to that binding protein can be created. Thus it would simply be required that a cDNA sequence be prepared and inserted into the strand containing the protein binding sequence before the assay method of the present invention could be initiated. Also, if the same assay procedure is to be conducted in a large number of repetitions, it would also be possible to insert the modified probe of the present invention into a cloning vector for cloning in large numbers to create a large reservoir of that modified probe for use in conducting this assay. Since the modified probe requires no particular treatment for use, other than its isolation from the organism in which it is cloned, it is possible to generate a large amount of the probe for use in the procedure.

The following examples further illustrate the present invention. These examples are not intended to limit the invention in any manner.

EXAMPLE 1

To prepare the binding protein sequence, the DNA of T7 bacteriophage was subjected to the restriction endonuclease Hea III. After complete digestion a fragment containing the strong promoters A1, A2, and A3 was resolved by electrophoresis and recovered from the agarose gel. These promoter sequences were used as the protein binding sequence. The recovered promoter fragments were ligated together to make high molecular weight polymers which were then spliced into the Sma I or the Hpa I sites of the plasmid vectors pNO1517 or pNO1523 by blunt end ligation using T4 DNA ligase directly, to create the modified probe. The modified probe was then cloned in *E. coli* strain MC1009, and prepared in bulk quantities.

The vectors pNO1517 and pNO1523 are derivatives of the plasmid pBR322 and therefore show sequence homology to it. Neither the vectors pNO1517 or pNO1523 nor the plasmid pBR322 include a sequence homologous to the protein binding sequences of the T7 bacteriophage.

As a test extract, DNA of the plasmid pBR322 was digested with the restriction endonuclease Taq1 and the two fragments of the highest molecular weight were resolved in an agarose gel and immobilized on a nitrocellose filter in the manner described by Southern, *J. Mol. Biol.*, 95:503–517(1975). As a control test extract, DNA from calf thymus was similarly immobilized. The nitrocellulose filters were then prewashed and hybridized to the denatured modified probes pNO1517 and pNO1523 carrying the T7 promoters in a buffer containing 2xSSC, 0.2% BSA, 0.2% ficoll, 0.2% PVP and 50 micrograms/ml denatured salmon sperm DNA. Before hybridization, the modified probe was denatured by heating to 80 degrees C. for ten minutes. After hybridization, the filters were successively washed first in a buffer of 0.5 ml of 2xSSC, containing 0.2% ficoll, 0.2% PVP at 65° C., secondly in a buffer of 1xSSC, also containing 0.2% ficoll and 0.2% PVP, and also at 65° C., and finally in RNA polymerase binding buffer (RNAPBB) at room temperature (22-25 degrees C.) for ten to thirty minutes each. The filters were then submerged in 0.2 ml of RNAPBB, which contains 10 mM Hepes(pH 7.2), 10 mM $MgCl_2$, 0.1 mM EDTA, 0.1M NaCl, and 50 micrograms per ml BSA, for two minutes at 37 degrees C. 25 micrograms of RNA polymerase from *E. coli* was then added and mixed with the filters. The filters were incubated at 37 degrees C. for 2-5 minutes. The filters were then removed, washed twice in 0.5 ml of RNAPBB at 25 degrees C. for 15 minutes. The filters were then transferred to 0.5 ml of RNAPBB and then 500 micrograms of anti-RNA polymerase antiserum prepared in rabbits was added. After 60 minutes at 37 degrees C., the filters were removed and washed twice in 0.5 ml of RNAPBB at 25 degrees C. for 15 minutes. The filters were then transferred to 0.5 ml of RNAPBB and then 25 micrograms of goat anti-rabbit IgG was added. After 60 minutes at 37 degrees C., the filters were removed and washed twice in 0.5 ml of RNAPBB. The filters were then allowed to react with 45 micrograms of horseradish peroxidase-rabbit antiperoxidase complex (PAP) in 100 microliter of RNAPBB at 37° C. for one hour. The filters were then washed twice with 0.5 ml of RNAPBB at 25° C. for 15 minutes each. The filters were then blotted dry and allowed to react with a peroxidase substrate solution (50 mM dibasic sodium phosphate, 25 mM citric acid, 0.04% O-phenylene diamine and 0.015% $H_2O_2$) at room temperature for 3 minutes.

Where the sample contained the pBR322 fragments which were the target sequences of the test, a bright yellowish brown color developed indicating a positive result. Where the sample contained no DNA or contained the DNA from the calf thymus, the observed result was negative and no intense color developed.

In this example, the binding protein, *E. coli* RNA polymerase was detected by an enzyme-linked double indirect immonoassay.

EXAMPLE 2

The same procedure as in Example 1 above was followed except that the pre-hybridiation wash and the hybridization were performed directly in RNAPBB and 0.1 mM dithiothreitol and the post-hybridization wash was in RNAPBB.

EXAMPLE 3

The same procedure was followed as in Example 2 except that the binding protein, RNA polymerase, was added directly with the modified probe during the hybridization step.

EXAMPLE 4

The same procedure was followed as in Example 1 above except that after the DNA fragments were resolved in agarose gel, they were recovered by electroelution and "dot-blotted" onto a nitrocellulose filter following the method described by Andre, *Schleicher & Schell Sequences, Application Update,* 1982.

EXAMPLE 5

The same procedure as in Example 1 above was used except that the second antiserum was conjugated to alkaline phosphatase. After 60 minutes at 37° C., the filters were removed, washed in RNABB and blotted dry. The filters were then allowed to react with an alkaline phosphatase substrate solution (1M diethanolamine (pH 9.8), 0.5 mM $MgCl_2$ and 15 mM p-nitrophenylphosphate) for color development. In this example, the binding protein was detected by an enzyme-linked indirect immunoassay.

EXAMPLE 6

The procedure as in Example 5 above was followed except that the prehybridization wash and the hybridization were performed in RNABB and 0.1 mM dithiothreitol and the post-hybridization wash was in RNABB.

EXAMPLE 7

The procedure as in Example 6 above was followed except that the binding protein, RNA polymerase, was added directly with the modified probe during the hybridization step.

EXAMPLE 8

The same procedure as in Example 2 above was followed except that after the binding of the rabbit anti-RNA polymerase antiserum and the subsequent washings, the filters were transferred to 0.5 ml RNABB containing an excess amount of *S. aureus* Cowan protein A-B galactosidase conjugate. After 60 minutes at 37° C., the filters were removed, washed in RNABB and blotted dry. The filters were then allowed to react with a B-galactosidase substrate solution (60 mM $Na_2HPO_4$, 40 mM $NaH_2PO_4$, 1 mM $MgSO_4$, 10 mM KCl, 2.7 ml per liter B-mercapto-ethanol, an 3 mg per ml O-nitrophenyl-B-D-galacto-pyranoside) for color development. In this example, the binding protein was detected by an enzyme-linked indirect immunoassay making use of protein A isolated from *S. aureus* Cowan instead of a second antiserum.

EXAMPLE 9

The sample procedure as in Example 8 above was followed except that the binding protein, RNA polymerase, was added directly with the modified probe during the hybridization step.

EXAMPLE 10

Hypothetically, the same procedure may be conducted as in Example 1, above, except that the goat anti-rabbit IgG may be linked to fluorescein. Following the binding of the goat anti-rabbit IgG and washings, the filter may then be observed under UV illumination. In samples containing the specific nucleotide sequence, fluorescence will be observed.

This is an example of a fluorescent marker-linked indirect immunoassay.

EXAMPLE 11

Hypothetically, the same procedure can be conducted as detailed in Example 1 above, except that the filter may be exposed to a goat anti-rabbit IgG which is linked to the enzyme peroxidase. After repeated washings, the filter is then submerged in a solution of peroxidase substrate for detection. Where the sample nucleotide extract contained in the specific nucleotide sequence it may be observed that an intense reddish brown color develops.

This is an example of an enzyme-linked indirect immunoassay for detection of the binding protein.

It is to be understood that modification of the above described method for carrying out the present invention is possible within the spirit of the present invention and thus the present invention should not be limited to the above described specification but should be interpreted in accordance with the following claims.

We claim:

1. A method for assaying for the presence of a specific nucleotide target sequence in a sample polynucleotide test extract comprising the steps of
   (a) isolating the sample polynucleotide extract in a test sample;
   (b) exposing the test sample to:
      (1) a polynucleotide modified probe comprising a cDNA sequence substantially complementary to the specific nucleotide sequence and a protein binding nucleotide sequence, and
      (2) a binding protein which specifically binds by a non-covalent bond to the binding sequence of the modified probe;
   (c) isolating the test sample to remove any constituents not bound to the sample polynucleotide extract and
   (d) conducting an assay of the test sample for the presence of the binding protein.

2. A method as claimed in either one of claim 1 wherein the step of isolating the sample polynucleotide extract comprises immobilizing the sample extract on an insoluable matrix.

3. A method as claimed in claim 1 wherein the protein binding sequence in the modified probe is selected from the group consisting of promoters, operators, specifically antigenic sequences, repetitive sequences, and histone binding sequences.

4. A method as claimed in claim 3 wherein the protein binding sequence in the modified probe is selected from the group consisting of lac-promoter, lac-operators, trp-promoters, T5 bacteriophage sequence, and T7 bacteriophage sequences.

5. A method as claimed in claim 1 wherein the binding protein is selected from the group consisting of DNA-polymerases, operon regulators, histones, and DNA modifying enzymes.

6. A method as claimed in claim 1 wherein the modified probe is created through the steps of:
   (a) preparing a cDNA sequence complementary to the specific nucleotide target sequence;
   (b) inserting the cDNA sequence into a cloning vector;
   (c) cloning the vector comprising the cDNA sequence;
   (d) isolating the cloned vectors comprising the cDNA sequence; and
   (e) inserting a protein binding nucleotide sequence into the cloned vector.

7. A method as claimed in claim 1 wherein the modified probe is created through the steps of:
   (a) isolating a vector comprising a protein binding sequence;
   (b) preparing a cDNA sequence complementary to the specific nucleotide target sequence; and
   (c) inserting the cDNA sequence into the vector comprising the protein binding sequence.

8. A method as claimed in claim 7 wherein the step of isolating a vector comprising a protein binding sequence comprises the steps of:
   (a) isolating a protein binding sequence from the DNA of one species;
   (b) inserting the protein binding sequence into a cloning vector from a second species;
   (c) cloning the cloning vector in a unicellular organism; and
   (d) isolating the cloned vector or a segment thereof comprising the protein binding sequence.

9. A method as claimed in claim 7 wherein the step of isolating a vector is accomplished by isolating a bacteriophage polynucleotide capable of serving as a vector which already comprises a protein binding sequence on it.

10. A method for assaying for the presence of a specific nucleotide target sequence in a sample polynucleotide test extract comprising the steps of
    (a) isolating the sample polynucleotide extract in a test sample;
    (b) exposing the test sample to:
       (1) a polynucleotide modified probe comprising a cDNA sequence substantially complementary to the specific nucleotide sequence and a specifically antigenic binding nucleotide sequence, and
       (2) an antiserum which specifically binds by a non-covalent bond to the specifically antigenic binding nucleotide sequence of the modified probe;
    (c) isolating the test sample to remove any constituents not bound to the sample polynucleotide extract and
    (d) conducting an assay of the test sample for the presence of the antiserum.

11. A method as claimed in claim 10 wherein the antiserum is anti-Z-DNA antiserum.

12. A method as claimed in claim 10 wherein the modified probe is created through the steps of:
    (a) preparing a cDNA sequence complementary to the specific nucleotide target sequence;
    (b) inserting the cDNA sequence into a cloning vector;
    (c) cloning the vector comprising the cDNA sequence;
    (d) isolating the cloned vectors comprising the cDNA sequence; and
    (e) inserting a specifically antigenic binding nucleotide sequence into the cloned vector.

13. A method as claimed in claim 12 wherein the modified probe is created through the steps of:
    (a) isolating a vector comprising a specifically antigenic binding nucleotide sequence;
    (b) preparing a cDNA sequence complementary to the specific nucleotide target sequence; and
    (c) inserting the cDNA sequence into the vector comprising the specifically antigenic binding nucleotide sequence.

14. A method as claimed in claim 13 wherein the step of isolating a vector comprising a specifically antigenic binding nucleotide sequence comprises the steps of:
    (a) isolating the specifically antigenic binding nucleotide sequence from the DNA of one species;
    (b) inserting the specifically antigenic binding nucleotide sequence into a cloning vector from a second species;
    (c) cloning the cloning vector in a unicellular organism; and (d) isolating the cloned vector or a segment thereof comprising the specifically antigenic binding nucleotide sequence.

15. A method as claimed in any one of claims 6, 7, or 13 further comprising the step of cloning the modified probe.

16. A method as claimed in either one of claim 1 or 10 wherein the step of exposing the test sample further comprises a separation step after the exposure to each reagent to remove unreacted constituents from the test sample.

17. A method as claimed in claim 1 wherein the step of conducting an assay for the binding protein comprises the steps of: exposing the test sample to an antiserum specific to the binding protein; and conducting an assay of the test sample for the presence of the antiserum.

18. A method as claimed in claim 17 wherein the antiserum is marker-linked and wherein the assay of the test sample is conducted by testing for the presence of the linked marker.

19. A method as claimed in claim 17 wherein the assay of the test sample is conducted through an indirect or double indirect marker-linked immunoassay for the antiserum.

20. A method as claimed in claims 18 or 19 wherein the marker is an enzyme.

21. A method as claimed in claim 10 wherein the anti-Z-DNA antiserum is marker-linked.

22. A method as claimed in claim 10 wherein the specifically antigenic sequence is a Z-DNA sequence and the antiserum is anti-Z-DNA antiserum.

23. A method as claimed in claim 10 wherein the specifically antigenic sequence is a sequence containing a rare and specifically antigenic nucleotide and the antiserum is an antiserum specific to a sequence containing that nucleotide.

24. A method as claimed in claim 23 wherein the rare nucleotide is selected from the group consisting of five-bromodeoxyuridine and five-iododeoxyuridine.

* * * * *